(12) United States Patent
Kweon et al.

(10) Patent No.: US 8,263,643 B2
(45) Date of Patent: Sep. 11, 2012

(54) POLYPHENOL COMPOUNDS WITH MODULATING NEUROTRANSMITTER RELEASE

(75) Inventors: Dae-Hyuk Kweon, Suwon-si (KR);
Yeon-Kyun Shin, Ames, IA (US);
Chang-Hwa Jung, Anyang-si (KR);
Yoo-Soo Yang, Seoul (KR)

(73) Assignee: Sungkyunkwan University Foundation for Corporate Collaboration, Suwon-Si (KR)

( * ) Notice: Subject to any disclaimer, the term of this patent is extended or adjusted under 35 U.S.C. 154(b) by 223 days.

(21) Appl. No.: 12/677,281

(22) PCT Filed: Mar. 12, 2008

(86) PCT No.: PCT/KR2008/001400
§ 371 (c)(1),
(2), (4) Date: Mar. 9, 2010

(87) PCT Pub. No.: WO2008/111796
PCT Pub. Date: Sep. 18, 2008

(65) Prior Publication Data
US 2011/0112181 A1    May 12, 2011

(30) Foreign Application Priority Data
Mar. 12, 2007  (KR) .................. 10-2007-0023991

(51) Int. Cl.
*A61K 31/366* (2006.01)
*A61K 31/352* (2006.01)
*A61K 31/122* (2006.01)

(52) U.S. Cl. .................. 514/453; 514/456; 514/685

(58) Field of Classification Search .................. 514/453, 514/456, 685
See application file for complete search history.

(56) References Cited

U.S. PATENT DOCUMENTS
7,410,659 B2 *  8/2008  Rosenbloom ................ 424/725

FOREIGN PATENT DOCUMENTS
| WO | 94/14414 A1 | 7/1994 |
| WO | 01/08652 A1 | 2/2001 |
| WO | 01/37788 A1 | 5/2001 |
| WO | 2006/070978 A1 | 7/2006 |

OTHER PUBLICATIONS

Blanes-Mira, C. et al., "A synthetic hexapeptide (Argireline) with antiwrinkle activity," International Journal of Cosmetic Science, 2002, vol. 24, pp. 303-310, Blackwell Science Ltd.
Guardia, Teresita et al. "Anti-inflammatory properties of plant flavonoids. Effects of rutin, quercetin and hesperidin on adjuvant arthritis in rat," Il Farmaco, Sep. 2001, vol. 56 (9), pp. 683-687, Elsevier Science S.A.
Weber, Thomas et al., "SNAREpins: Minimal machinery for membrane fusion," Cell, Mar. 20, 1998, vol. 92, pp. 759-772, Cell Press.
International Search Report dated Jun. 16, 2008 for PCT/KR2008/001400.

* cited by examiner

*Primary Examiner* — Raymond Henley, III
(74) *Attorney, Agent, or Firm* — NSIP Law

(57) ABSTRACT

Disclosed is a composition for modulating the release of a neurotransmitter, which includes naturally extracted polyphenols as an active ingredient. The disclosed composition suppresses the formation of a SNARE complex, thereby modulating the release of a neurotransmitter, and thus can be used as a modulator for a reaction within a cell related to the SNARE complex. Such an inhibitor of the SNARE complex formation can be used as a composition for reducing wrinkles and relieving pain.

3 Claims, 8 Drawing Sheets

FIG. 1
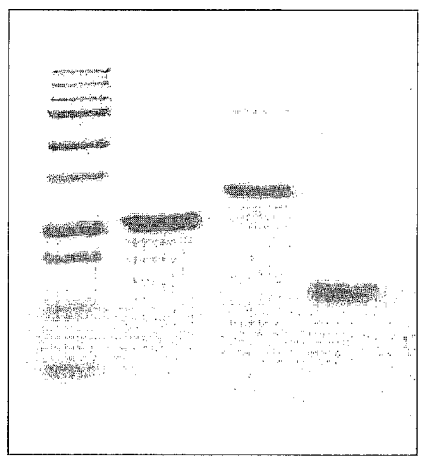
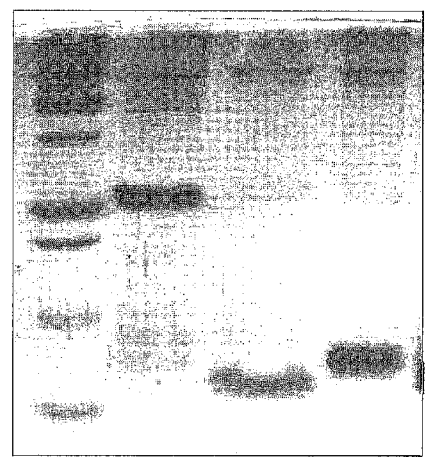
SNAP25 Sytaxin1A VAMP2          SNAP25   SynH3   Vps

In the presence of SNARE inhibitor
In the absence of SNARE inhibitor

POLYPHENOL COMPOUNDS WITH MODULATING NEUROTRANSMITTER RELEASE

TECHNICAL FIELD

The present invention is related to compounds that modulate the release of neurotransmitters from neuronal cells, and compositions comprising the same.

BACKGROUND ART

In the upper portion of a muscle, there is a neuromuscular junction for controlling the relaxation and contraction of the muscle, and also, the nerve terminal is charged with a synaptic vesicle. The muscles contract by receiving a message of a neurotransmitter transmitted from the inside of a kind of neuron. For the release of such a neurotransmitter, a receptor complex, which is called SNARE (soluble N-ethylmaleimide-sensitive factor attachment protein receptor; SNAP Receptor), is required, and the receptor complex allows synaptic vesicles to merge with presynaptic membrane.

More specifically, for the release of a neurotransmitter, a synaptic vesicle containing the neurotransmitter is required to be fused with a presynaptic membrane so that a passage between two boundaries can be formed. Herein, a fundamental force for such membrane fusion is provided by SNARE complexes comprising three kinds of proteins. Particularly, when a release passage of a neurotransmitter is generated by membrane fusion between a synaptic vesicle and a presynaptic membrane, a t-SNARE complex (a complex of a syntaxin-1a protein, and a SNAP-25 protein) attached to a target membrane forms a parallel coiled with a v-SNARE attached to a vesicle, and herein, such SNARE proteins are twisted in a spiral shape.

In the membrane fusion, rearrangement of a lipid bilayer, which is widely known in the art, occurs. Since biomembranes strongly repel against each other, the membranes cannot be automatically merged, and thus a strong external force is required to overcome the repulsive force between the membranes. Herein, SNARE proteins generate such a strong force enough to overcome the repulsive force between the membranes. In other words, the formation of a SNARE complex is a force generator to overcome a repulsive power between membranes, and a main action in exocytosis including release of a neurotransmitter (refer to Weber et al., Cell, 92, 759-772 (1998)).

If a SNARE receptor complex is somewhat unstable, a carrier cannot actively secrete a neurotransmitter, and thus muscle contraction decreases, which indicates that wrinkle formation decreases (see FIG. 8).

On the basis of such a mechanism, many substances for suppressing wrinkle formation have been researched and commercialized.

BoNT (Botulinum neurotoxin, hereinafter, referred to as a 'botox') is a protease for cleavage of a SNARE protein, which is a main protein concerned in the release of a neurotransmitter. A botox cleaves a SNARE protein, and thus blocks neurotransmission, which results in paralysis of botox-penetrated muscle cells.

Also, in International Journal of Cosmetic Science 24 (Blanes-Mira et al., 303-310, 2002), argireline (so-called "applicable botox"), which is a synthesized hexapeptide, is described. Such a hexapeptide has an amino acid sequence of EEMQRR, and the sequence corresponds to an amino acid sequence of an N-terminal of SNAP-25. In other words, it can be said that the hexapeptide is a kind of competitive inhibitor inhibiting neurotransmission because a small hexapeptide takes the position where intact SNAP-25 is bound, thereby preventing the intact SNAP-25 from being bound to other SNARE proteins such as syntaxin 1a and VAMP2.

Argireline, that is, a chief ingredient of an applicable botox product, currently has a disadvantage in that its effect is not reliable, its price is unfavorable due to a characteristic of synthetic peptide, and it is not consumer-friendly.

On the other hand, it is determined that a neurotransmitter inhibitor developed by using a naturally extracted or synthesized polyphenol compound can be easily industrially applicable, compared to a peptide substance, because such inhibitors are much less expensive than synthetic peptide, and a finally-developed product of the inhibitor can be friendly and attractive to a consumer because they are natural materials.

Accordingly, the inventors of the present invention have completed this invention by verifying several effects by using a polyphenol compound, such as bondability between polyphenol and a SNARE protein, inhibition of membrane fusion, and suppression of SNARE complex formation on SDS-PAGE.

DISCLOSURE

Technical Problem

Therefore, the present invention has been made in view of the above-mentioned problems, and the present invention provides a SNARE inhibiting composition including a polyphenol compound capable of modulating the release of a neurotransmitter as an active ingredient.

Also, the present invention provides a neurotransmitter inhibiting composition including the polyphenol compound as an active ingredient.

Also, the present invention provides a skin-wrinkle reducing cosmetic composition for inhibiting neurotransmission, which includes the polyphenol compound as an active ingredient.

Also, the present invention provides a pain-relieving pharmaceutical composition including the polyphenol compound as an active ingredient.

Technical Solution

According to an aspect of the present invention, SNARE inhibiting compositions are provided containing certain polyphenol compounds.

More specifically, the present invention provides a SNARE inhibiting composition including one or at least two kinds of materials selected from kaempferol, quercetin, myricetin, luteolin, delphinidin, cyanidin, butein, ellagic acid, and a derivative thereof as active ingredients.

The present inventors have consistently researched 39 kinds of polyphenols from among naturally extracted polyphenols in order to develop an excellent modulator of SNARE complex formation, and as a result, have found that from among naturally extracted active ingredients, polyphenol compounds, such as kaempferol, quercetin, myricetin, luteolin, delphinidin, cyanidin, butein, and ellagic acid, inhibit the formation of a SNARE complex concerned in a pathway of neurotransmission (see Table 1). A membrane fusion inhibiting effect and a neurotransmitter release inhibiting effect by the polyphenol compounds were measured based on the fact that a neurotransmitter is secreted by an action of a SNARE protein, and titer of the SNARE protein can be measured by using a membrane fusion phenomenon. As a result, it has been found that the compounds have the best effect on the inhibition of membrane fusion and the modulation of transmitter release.

The polyphenol compound has a structural property closely connected to the number and position of free hydroxides included in each compound, and a molecule size of the compound. Specifically, a derivative of the compound has a structure similar to the compound, in which sugar, a methyl group, etc. are bound to hydroxides of A and C rings, except a B ring of high activity, in the structure of the compound, and thus can show activity similar to the compound.

Such an active ingredient can be obtained from nature by extraction from nature, or can be obtained by a synthesis method widely known in the field of organic chemical synthesis.

In a SNARE inhibiting composition of the present invention, an active ingredient can be solely used, and a combination of at least two active ingredients can be used. Such a combination can be easily understood by one skilled in the art, and is not particularly limited in the present invention.

According to another aspect of the present invention, there is provided a neurotransmitter inhibiting composition including one or at least two kinds of materials selected from kaempferol, quercetin, myricetin, luteolin, delphinidin, cyanidin, butein, ellagic acid, and a derivative thereof as an active ingredient.

The above active ingredient suppresses the formation of a SNARE complex, thereby playing a role of inhibiting the release of a neurotransmitter, which can be verified by release inhibition of norepinephrine (that is, a dopamine derivative) in a PCI cell.

In a neurotransmitter inhibiting composition of the present invention, an active ingredient can be solely used, and also, a combination of at least two active ingredients can be used. Such a combination can be easily understood by one skilled in the art, and is not particularly limited in the present invention.

According to a further aspect of the present invention, there is provided a skin-wrinkle reducing cosmetic composition including one or at least two kinds of materials selected from kaempferol, quercetin, myricetin, luteolin, delphinidin, cyanidin, butein, ellagic acid, and a derivative thereof as an active ingredient.

An active ingredient of the present invention inhibits the formation of a SNARE complex, thereby preventing a neurotransmitter from being actively secreted, which results in a skin-wrinkle reducing effect by reduction of muscle contraction. Through actual experiments on a wrinkle reducing effect, it has been verified that there exists an actual wrinkle reducing effect.

The content of active ingredient of the present invention may be 0.0001 to 10.0 wt % based on the total weight of the skin-wrinkle reducing cosmetic composition. If the content is out of the range, a skin-wrinkle reducing effect cannot be significantly achieved.

The active ingredient of the present invention can be solely used, and also, a combination of at least two active ingredients can be used, within the above described range. Such a combination can be easily understood by one skilled in the art, and is not particularly limited in the present invention.

The cosmetic composition may be prepared into a formulation selected from the group including solution, suspension, emulsion, paste, cream, gel, lotion, powder, soap, surfactant containing cleaning, oil, powder foundation, emulsion foundation, wax foundation, spray, etc.

When the formulation of the present invention is a paste, cream, or gel, examples of a carrier ingredient may include, but are not limited to, animal oil, vegetable oil, wax, paraffin, starch, tragacanth, a cellulose derivative, polyethylene glycol, silicon, bentonite, silica, talc, zinc oxide, etc. may be used.

When the formulation of the present invention is powder or spray, examples of a carrier ingredient may include, but are not limited to lactose, talc, silica, aluminum hydroxide, calcium silicate, or polyamide powder, and especially, the spray formulation may further include a propellant, such as chloro fluoro hydrocarbon, propane/butane, or dimethyl ether, but the present invention is not limited thereto.

When the formulation of the present invention is a solution or emulsion, examples of a carrier ingredient may include, but are not limited to, a solvent, a solubilizer or an emulsifier (for example, water, ethanol, isopropanol, ethyl carbonate, ethyl acetate, benzyl alcohol, benzyl benzoate, propylene glycol, 1,3-butylglycol oil, glycerol aliphatic ester, polyethylene glycol, or sorbitan fatty acid ester).

When the formulation of the present invention is a suspension, examples of a carrier ingredient may include, but are not limited to, a liquid diluent (such as water, ethanol, or propylene glycol), a suspension (such as ethoxylated isostearyl alcohol, polyoxyethylene sorbitol ester, and polyoxyethylene sorbitan ester), microcrystalline cellulose, aluminum metahydroxide, bentonite, agar, or tragacanth, etc.

When the formulation of the present invention is a surfactant containing cleansing, examples of a carrier ingredient may include, but are not limited to, aliphatic alcohol sulfate, aliphatic alcohol ether sulfate, sulfosuccinic acid monoester, isethionate, an imidazolinium derivative, methyl taurate, sarcosinate, fatty acid amide ether sulfate, alkyl amido betaine, aliphatic alcohol, fatty acid glyceride, fatty acid diethanolamide, vegetable oil, lanolin derivative, ethoxylated glycerol fatty acid ester, etc.

According to a still further aspect of the present invention, there is provided a pain relieving pharmaceutical composition containing a carrier, a diluent, or an excipient (which are pharmaceutical acceptable), and including one or at least two kinds of materials selected from kaempferol, quercetin, myricetin, luteolin, delphinidin, cyanidin, butein, ellagic acid, and a derivative thereof as an active ingredient.

An active ingredient of the present invention suppresses the formation of a SNARE complex, thereby playing a role of preventing a neurotransmitter from being secreted, and thus can be used as a pain relieving pharmaceutical composition, such as an analgesic.

The content of active ingredient of the present invention may be 0.0001 to 50 wt % based on the total weight of the pain relieving pharmaceutical composition. If the content is out of the range, a pain relieving effect cannot be significantly achieved. The active ingredient of the present invention can be solely used, and also, a combination of at least two active ingredients can be used, within the above described range. Such a combination can be easily understood by one skilled in the art, and is not particularly limited in the present invention.

The polyphenol compound composition according to the present invention may be prepared as any conventional formulations known in the art, and the formulations may include oral forms (such as powder, granule, tablet, capsule, suspension, emulsion, syrup, aerosol, etc.), an external application form, a suppository, or a sterile injection solution according to a conventional method of preparing a pharmaceutical composition.

A carrier, a diluent, or an excipient, that may be included in the pharmaceutical composition according to the present invention, varies according to formations, and examples of the carrier, the diluent, or the excipient may include lactose, dextrose, sucrose, sorbitol, mannitol, xylitol, erythritol, maltitol, starch, acacia senegal gum, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, mineral oil, etc.

Advantageous Effects

As can be seen from the foregoing, a polyphenol compound composition according to the present invention suppresses the formation of a SNARE complex, thereby modulating the release of a neurotransmitter, and thus can be used as a modulator for a reaction within a cell related to the SNARE complex. The SNARE complex formation inhibitor according to the present invention can be used as a composition for reducing wrinkles and relieving pain.

DESCRIPTION OF DRAWINGS

The foregoing and other objects, features and advantages of the present invention will become more apparent from the following detailed description when taken in conjunction with the accompanying drawings in which:

FIG. 1 shows the results of SDS-PAGE (Sodium dodecyl sulfate-polyacyamide gel electrophoresis) analysis on SNARE proteins obtained through expression and purification of a protein in recombinant *E. coli*.

FIG. 3 shows membrane fusion graphs when 8 representative kinds of polyphenol compounds are used, in which red circles indicate the route of a control reaction.

FIG. 4 shows the observation results on inhibition of neurotransmitter release when a normal PC12 cell is treated with a polyphenol compound. FIG. 5 shows that, after a neurotransmitter charged in presynaptic membrane was compulsorily released by potassium with high concentration, the formation of a SNARE complex within a cell is inhibited by treatment of a polyphenol compound, thereby significantly inhibiting the release of a neurotransmitter.

MODE FOR INVENTION

Figure 2:
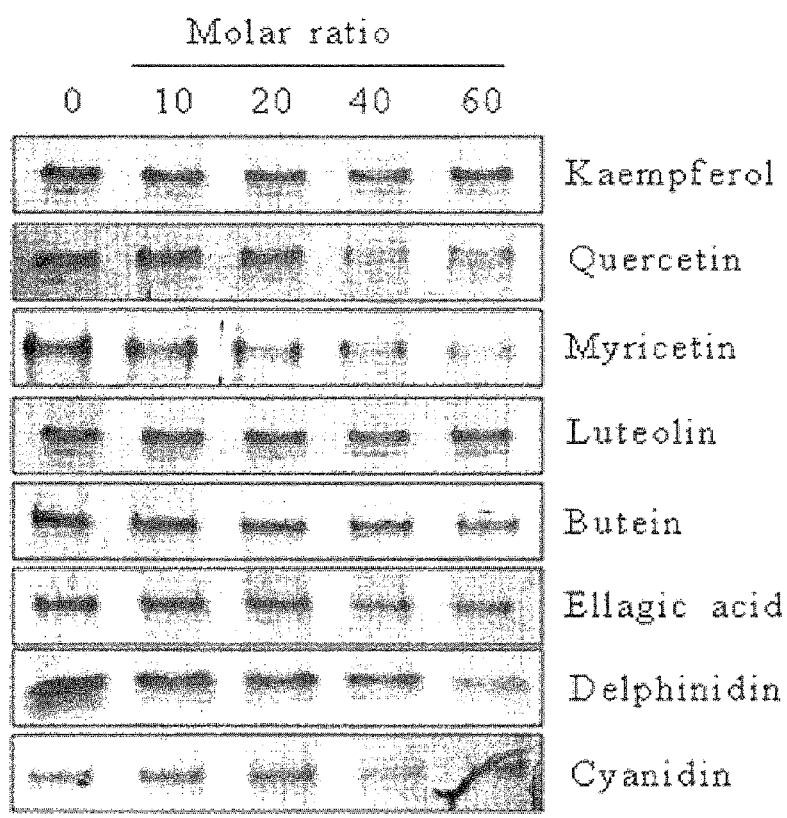
FIG. 2 shows the results of SDS-PAGE analysis for determining a SNARE complex formation inhibiting effect by a polyphenol compound according to the present invention (the numbers on the top of the gel photo indicate the molar concentration ratios of a SNARE protein to treated polyphenol, and the names on the right side indicate polyphenol compounds, respectively).

Reference will now be made in detail to the preferred embodiments of the present invention. It is to be understood that the following examples are illustrative only, and the scope of the present invention is not limited thereto.

Example 1

SDS-PAGE (Sodium Dodecyl Sulfate-Polyacrylamide Gel Electrophoresis) Analysis

A SNARE complex is strong enough so as not to be untwisted by SDS. On the basis of such a property, a SDS-PAGE analysis was performed in order to determine the formation of a SNARE complex. Polyphenol compounds used in the present Example were purchased from Sigma-Aldrich, Wako Chemical, and Extrasynthese.

In order to produce SNARE proteins, SNARE proteins, such as, SNAP25 (NM011428), syntaxin 1A (AF217197), VAMP2 (NM012663), SynH3 (AF217197), and Vps (NM012663), were purified in biologically transformed *E. coli* (Codon (+) RIL, Novagen).

It was determined whether the formation of a complex by mixing SNAP25, SynH3, and Vps (which are SNARE proteins purified in biologically transformed *E. coli* as described above) at a molar concentration (40 μM) of 1:1:1 was inhibited or not by the addition of a polyphenol compound. 10 μl of each protein was dripped in a 1 ml tube by a predetermined interval, and 100 μM of a polyphenol compound was added. Then, the materials were quickly mixed by a vortex, and were reacted at room temperature for 30 minutes. After the completion of the reaction, a sample buffer solution was added to deactivate the reaction, and whether a SNARE complex was formed or not was determined on 12% SDS-PAGE by electrophoresis (see FIG. 1). Table 1 shows the results.

The polyphenol compound inhibiting the formation of a SNARE complex has a structural property closely connected to the number and position of free hydroxides included in each compound, and a molecule size of the compound. Thus, on the basis of the above results, it is determined that a derivative of the compound having a structure where sugar, a methyl group, etc. are bound to hydroxides of A and C rings (except B ring of high activity) of the structure of the compound can show activity similar to the compound.

TABLE 1

Phenolic compound inhibiting formation of SNARE complex

| Family | Compound | SNARE complex formation (%) | Family | Compound | SNARE complex formation (%) |
|---|---|---|---|---|---|
|  | Control | 100 |  |  |  |
| Flavanol | (+)-Catechin | 105.02 ± 11.37 | Flavonol | Kaempferol | 100.13 ± 7.16 |
|  | (−)-Epicatechin | 114.55 ± 5.00 |  | Quercetin | 79.80 ± 10.77* |
|  |  |  |  | Quercitrin | 92.18 ± 9.59 |
|  | EGCG | 112.38 ± 10.43 |  | Rutin | 92.86 ± 9.53 |
|  |  |  |  | Fisetin | 90.14 ± 10.42 |
|  |  |  |  | Myricetin | 72.13 ± 10.13* |
| Flavanone | Naringin | 105.02 ± 11.37 | Flavone | Apigenin | 96.94 ± 7.99 |
|  | Hesperetin | 114.55 ± 5.00 |  | Luteolin | 86.23 ± 8.14* |
|  | Hesperidin | 112.38 ± 10.43 |  | Chrysin | 98.12 ± 6.56 |
|  | Taxifolin |  |  |  |  |
| Isoflavone | Genistein | 96.76 ± 8.91 | Tannin | Ellagic acid | 87.54 ± 9.50* |
|  | Daidzein | 104.06 ± 24.43 |  |  |  |

TABLE 1-continued

Phenolic compound inhibiting formation of SNARE complex

| Family | Compound | SNARE complex formation (%) | Family | Compound | SNARE complex formation (%) |
|---|---|---|---|---|---|
| Chalcone | Butein | 88.45 ± 7.09* | Dihydrochalcone | Phloridzin | 115.19 ± 23.74 |
| Anthocyanidins | Malvidin | 97.42 ± 6.31 | Lignan | Gomisin A | 97.99 ± 0.87 |
| | Cyanidin | 67.12 ± 20.31* | | Gomisiin N | 99.04 ± 5.17 |
| | Pelargonidin | 95.61 ± 3.10 | | Schizandrin | 107.60 ± 13.30 |
| | Delphinidin | 60.53 ± 18.88* | | | |
| Benzoic acidderivatives | Ferulic acid | 93.38 ± 14.39 | Phenylpropanoids | Gentisic acid | 100.16 ± 2.19 |
| | Caffeic acid | 93.33 ± 12.20 | | | |
| | p-Coumaric acid | 91.21 ± 11.99 | | Protocate chuic acid | 98.38 ± 4.56 |
| | Chlorogenic acid | 100.78 ± 13.62 | | Vanillic acid | 97.23 ± 5.70 |
| | Trans-cinnamic acid | 106.78 ± 30.15 | | Syringic acid | 92.25 ± 5.92 |

[phenolic compound]:SNAP-25 = 1:1 and equimolar concentrations of SNARE proteins (10 μM each) were mixed together.
*p < 0.05, compared with the control.

The concentration of each polyphenol compound used in the experiment was 100 μM.

FIG. 2 shows the measurement results of a SNARE complex formation inhibiting effect by 8 kinds of polyphenol compounds, that is, kaempferol, quercetin, myricetin, luteolin, butein, ellagic acid, delphinidin, and cyanidin (which were selected from the results as noted in Table 1) at each concentration.

As shown in FIG. 2, it was determined that the extracts can concentration-dependently effectively inhibit the formation of a SNARE complex. In FIG. 2, the numbers on the top of the gel photo indicate the concentrations of treated polyphenol, and the names on the right side indicate polyphenol compounds, respectively.

In the below Table 2, the numerical values of the results shown in FIG. 2 are noted, and the values indicate the molar concentration ratio ($IR_{50}$) of each selected polyphenol compound, which is required for inhibiting the formation of a SNARE complex by 50%. According to the measurement results, myricetin, cyanidin, delphinidin, quercetin, kaempferol, butein, and ellagic acid can inhibit the formation of a SNARE complex by 50% at a low concentration.

TABLE 2 molar concentration ratio ($IR_{50}$) of selected polyphenol compound, which is required for inhibiting the formation of a SNARE complex by 50%

| Phenolic compounds | Ratio for inhibition by 50% ($IR_{50}$)[a] |
|---|---|
| Kaempferol | >60[b] |
| Quercetin | 24.9 |
| Myricetin | 14.9 |
| Luteolin | 38.2 |
| Butein | 30.5 |
| Ellagic acid | 27.8 |
| Delphinidin | 12.2 |
| Cyanidin | 22.3 |

[a]$IR_{50}$ indicates the molar concentration ratio ($IR_{50}$) of a polyphenol compound, which is required for inhibiting the formation of a SNARE complex by 50%.
[b]inhibition ratio of the tested compound (phenolic compound: SNAP-25) did not reached to 50%.
The above data is based on an average value of at least three measurements.

Example 2

A Membrane Fusion Inhibiting Effect

In order to find an inhibitor for inhibiting a membrane fusion, a membrane fusion inhibiting effect of each of 8 kinds of selected polyphenol compounds was tested.

In order to produce SNARE proteins, SNARE proteins, such as SNAP25 (NM011428), syntaxin 1A (AF217197), and VAMP2 (NM012663), were purified in biologically transformed *E. coli* (Codon (+) RIL, Novagen).

In order to prepare liposome (fine membrane) marked with a fluorescent substance, POPC (62 mol %), DOPS (35 mol %), NBD-PS (1.5 mol %) and a fluorescent substance Rhodamin-PE (1.5 mol %) were mixed to obtain 10 mM of liposome (v-vesicle). Also, in order to prepare a liposome not marked with a fluorescent substance, DOPS and POPC were mixed in a molar concentration ratio of 35:65 to obtain 50 mM of liposome (t-vesicle). In order to prepare a complex of the purified SNAP25 and syntaxin 1a, the SNAP25 and the syntaxin 1a were mixed in a molar concentration ratio of 1:1, and then were reacted at room temperature for 1 hour. Then, the resultant mixture and the liposome not marked with a fluorescent substance were mixed in a molar ratio of 100:1. The VAMP2 and the liposome marked with a fluorescent substance were mixed in a molar ratio of 50:1. Then, each of the two kinds of liposomes was dialyzed by using 10 kDa dialyzing membrane through agitation at 4° C. for 24 hours, and the liposomes were mixed in a ratio of 3:7 (v-vesicle t-visicle). Next, fluorescence was measured by using a fluorometer (SpectraMax M2 manufactured by Molecular Device).

The below Table 3 shows the degree of membrane fusion inhibition by respective tested polyphenol compounds.

TABLE 3

Phenolic compound inhibiting membrane fusion caused by SNARE (20 µM)

| | | | | | |
|---|---|---|---|---|---|
| Flavanol | (+)-Catechin | 89.15 ± 1.19 | Flavonol | Kaempferol | 108.46 ± 5.00 |
| | (−)-Epicatechin | 97.98 ± 1.50 | | Quercetin | 33.41 ± 2.24* |
| | | | | Quercitrin | 85.95 ± 26.14 |
| | EGCG (Epigallocatechin gallate) | 57.59 ± 3.39* | | Spiraeoside | 106.75 ± 6.72 |
| | | | | Rutin | 96.67 ± 10.64 |
| | | | | Fisetin | 32.06 ± 4.14* |
| | | | | Myricetin | 43.92 ± 8.38* |
| Flavanone | Naringin | 107.04 ± 2.89 | Flavone | Apigenin | 96.94 ± 7.99 |
| | Hesperetin | 107.37 ± 2.29 | | Luteolin | 65.52 ± 2.09* |
| | Hesperidin | 124.11 ± 15.01 | | Chrysin | 120.90 ± 1.27 |
| | Taxifolin | 109.23 ± 3.92 | | Gossypin | 103.19 ± 9.01 |
| Isoflavone | Genistein | 119.21 ± 18.09 | Tannin | Ellagic acid | 22.04 ± 2.05* |
| | Daidzein | 112.72 ± 13.11 | | | |
| Chalcone | Butein | 16.89 ± 2.98* | Dihydrochalcone | Phloridzin | 86.26 ± 3.87 |
| Anthocyanidins | Malvidin | 115.79 ± 5.97 | Lignan | Gomisin A | 79.63 ± 7.58 |
| | Cyanidin | 7.23 ± 1.08* | | Gomisiin N | 92.31 ± 2.37 |
| | Pelargonidin | 92.39 ± 3.38 | | Schizandrin | 116.09 ± 5.52 |
| | Delphinidin | 37.55 ± 3.45* | | | |
| Benzoic acid derivatives | Ferulic acid | 118.02 ± 2.79 | Phenylpropanoids | Gentisic acid | 96.68 ± 2.38 |
| | Caffeic acid | 124.73 ± 7.45 | | | |
| | p-Coumaric acid | 123.19 ± 14.3 | | Protocatechuic acid | 104.20 ± 8.19 |
| | Chlorogenic acid | 133.94 ± 1.49 | | Vanillic acid | 99.59 ± 7.63 |
| | Trans-cinnamic acid | 107.50 ± 10.60 | | Syringic acid | 78.25 ± 2.47 |

*$p < 0.05$, compared to control group.

Herein, 100% indicates the degree of membrane fusion in the state where no inhibitor was added. As the value is smaller, the inhibiting degree is higher.

Figure 3:
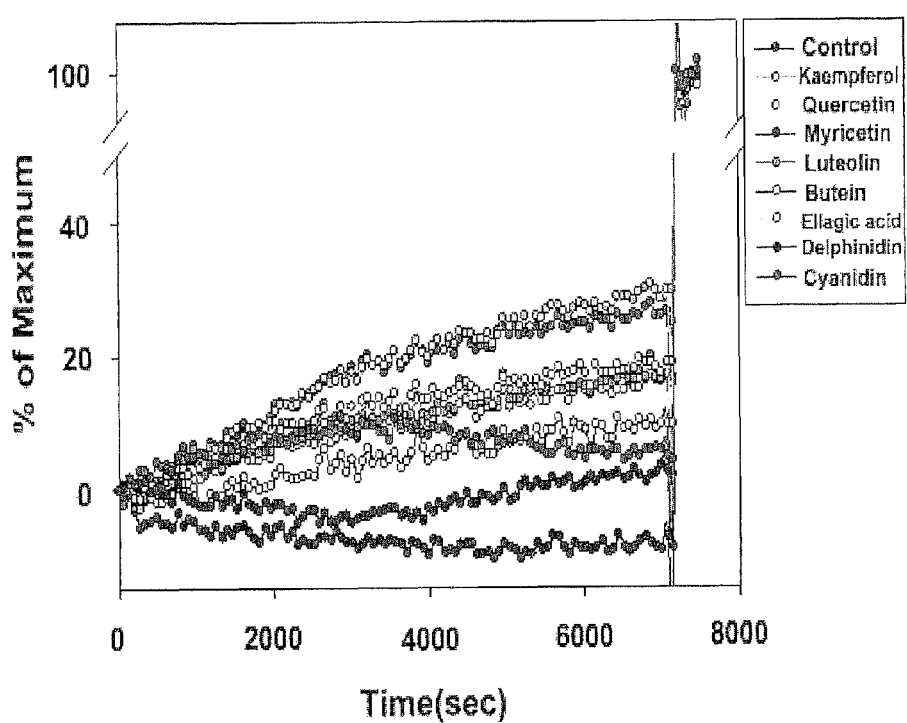
FIG. 3 shows membrane fusion assay inhibiting effects, which is for finding out a SNARE complex formation inhibitor from among polyphenol compounds of the present invention.

FIG. 3 shows membrane fusion graphs when 8 representative kinds of polyphenol compounds are used. In FIG. 3, the fluorescence intensity indicates membrane fusion between SNARE proteins, and thus low fluorescence intensity indicates an excellent membrane fusion inhibiting effect.

Red circles indicate the route of a control reaction. When only ethanol, instead of a compound, was added, the reaction reached up to about 30% of the maximum of fluorescence intensity, and also, reactions by most of polyphenol compounds show routes similar to the control reaction.

FIG. 3 shows test results on 8 selected kinds of polyphenol compounds, and herein the test was carried out in order to find out a membrane fusion inhibitor by a polyphenol compound. It was determined that kaempferol quercetin, myricetin, luteolin, butein, and ellagic acid (which were used in the test) can reduce membrane fusion. Accordingly, as noted in Table 2, kaempferol, quercetin, myricetin, luteolin, butein, and ellagic acid can inhibit the formation of a SNARE complex.

The below Table 4 shows the molar concentration ratio of each of representative 8 kinds of polyphenol compounds (to a SNARE protein), which is required for inhibiting the membrane fusion by 50%.

TABLE 4 molar concentration ratio ($IR_{50}$) of selected polyphenol compound, which is required for inhibiting the membrane fusion by 50%

| Phenolic compounds | Ratio for inhibition by 50% ($IR_{50}$)[a] |
|---|---|
| Kaempferol | >20[b] |
| Quercetin | 2.87 |
| Myricetin | 0.79 |
| Luteolin | 4.02 |
| Butein | 0.81 |
| Ellagic acid | 7.31 |
| Delphinidin | 0.86 |
| Cyanidin | 0.80 |

[a]$IR_{50}$ indicates the molar concentration ratio ($IR_{50}$) of a polyphenol compound, which is required for inhibiting the membrane fusion by 50%.
[b]inhibition ratio of the tested compound (phenolic compound: SNAP-25) did not reached to 50%.
The above data is based on an average value of at least three measurements.

Example 3

Inhibition of Neurotransmitter Release from PC12 Cell

PC12 cells were cultured in a Ham's F12K medium where 10% fetal calf serum, 5% fetal bovine serum, and antibiotics were added in a collagen-coated plate (60 mm dish). In sub-culture, after sucking of the medium, 2 ml of PBS was added and cells were separated from a dish wall through pipetting. Then, centrifugation with 1,000×g for 5 minutes was carried out to obtain cells. A new medium was introduced, and a cell pellet was dispersed through pipetting and was loaded onto a new culture plate. And culture was carried out at 37° C. in a culture medium providing 5% $CO_2$ gas. [$^3$H]-norepinephrine used for the experiment was purchased from Amersham. After sucking of the medium in the plate of PC12 cells, PBS was added and cells were separated from a plate wall. Then, the number of cells was measured by a hemacytometer, and the cells were dispersedly inoculated into a new medium at a concentration of 2×10⁵ cell/ml. After 24 hours, a buffer solution ([³H]—NE, 1.5 μCi/ml) for assay of norepinephrine was added, and then the cells were induced in a carbon dioxide incubator for 90 minutes. After the reaction, the buffer solution was removed and the cells were washed three times with PBS. Then, a new medium and each polyphenol compound were loaded and a reaction was performed for 30 minute. After the removal of the medium, A high concentration K⁺ buffer solution was added, and culture was performed in a carbon dioxide incubator for 12 minutes. Then the supernatant was obtained to determine whether the release of [³H]-norepinephrine is inhibited or not through scintillation counter.

Figure 4:
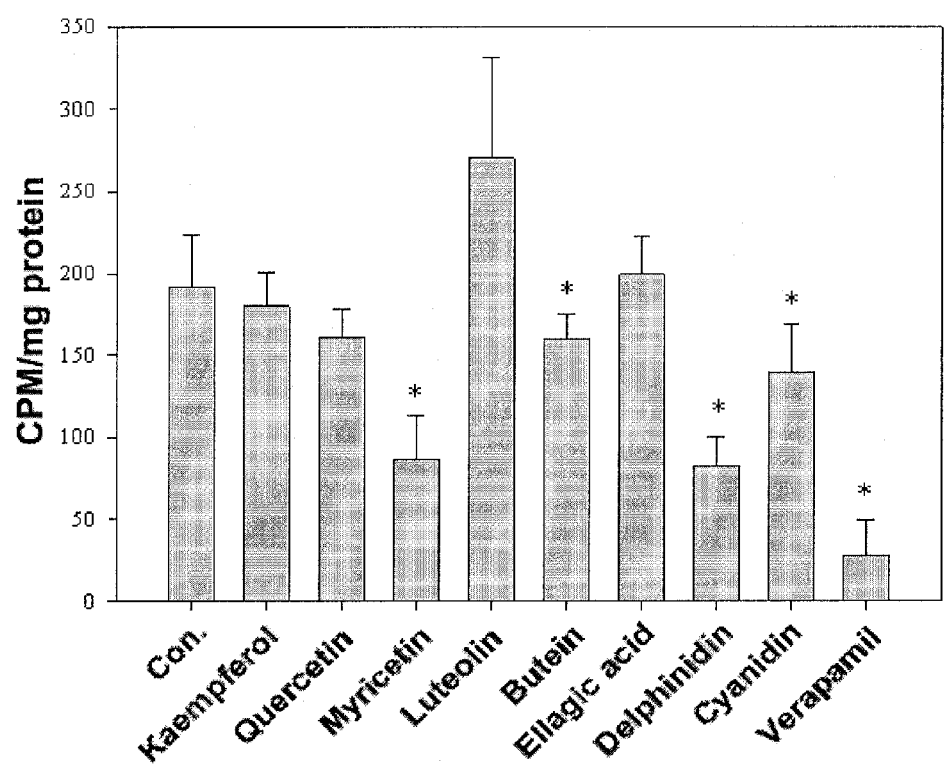
FIGS. 4 and 5 show a neurotransmitter inhibiting effect in a PC12 cell by a polyphenol compound of the present invention.
Figure 5:
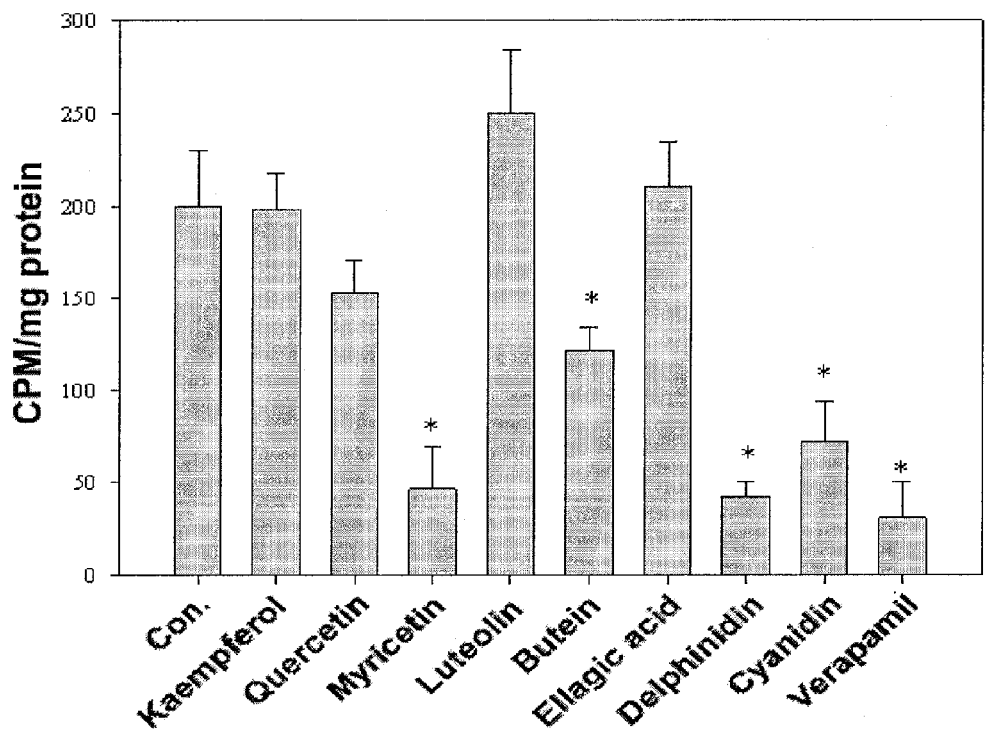

In the same manner, it was determined whether a polyphenol compound inhibits the release of norepinephrine (a derivative of dopamine) within PC12 cells or not. FIGS. 4 and 5 show the results. FIG. 4 shows the observation results on inhibition of neurotransmitter release when normal PC12 cells are treated with a polyphenol compound. All 8 kinds of compounds used for the experiment inhibited the neurotransmitter release, and especially, myricetin, delphinidin, cyanidin, and butein showed relatively high norepinephrine release inhibiting effects. Herein, verepamil was selected as a control group and was used to find out efficacy of a selected polyphenol compound. Verapamil is a calcium channel blocker which is also widely used as a medicine. Compared to verapamil inhibiting the release of a neurotransmitter by blocking the inflow of calcium, a polyphenol compound according to the present invention directly inhibits the formation of a SNARE complex. An action mechanism of the verapamil is different from the polyphenol compound, but has the same final efficacy to the polyphenol compound. Therefore, the verapamil was treated as a control group for efficacy comparison. FIG. 5 shows that, after a neurotransmitter charged in presynaptic membrane was compulsorily released by potassium with high concentration, the formation of a SNARE complex within a cell is inhibited by treatment of a polyphenol compound, thereby significantly inhibiting the release of a neurotransmitter.

Figure 6:
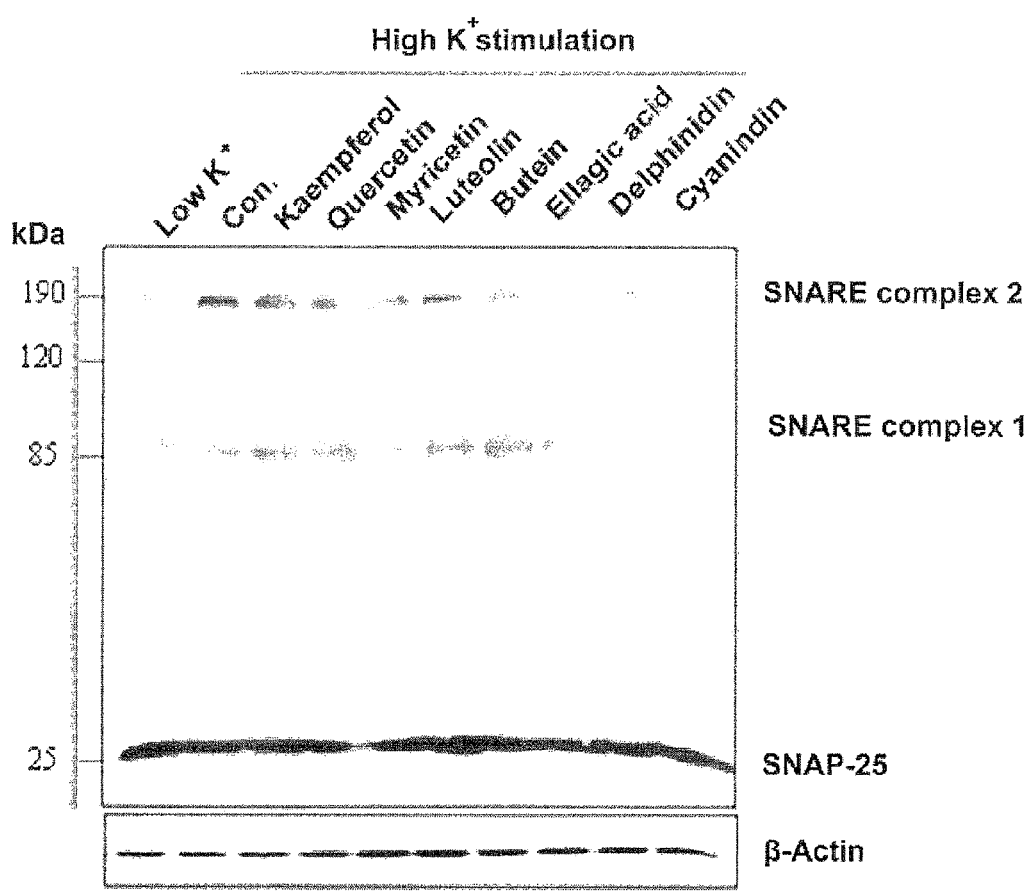
FIG. 6 shows Western blot results illustrating that a neurotransmitter release inhibiting effect in a PC12 cell by a polyphenol compound according to the present invention was caused by inhibiting the formation of a SNARE complex.
Figure 7:
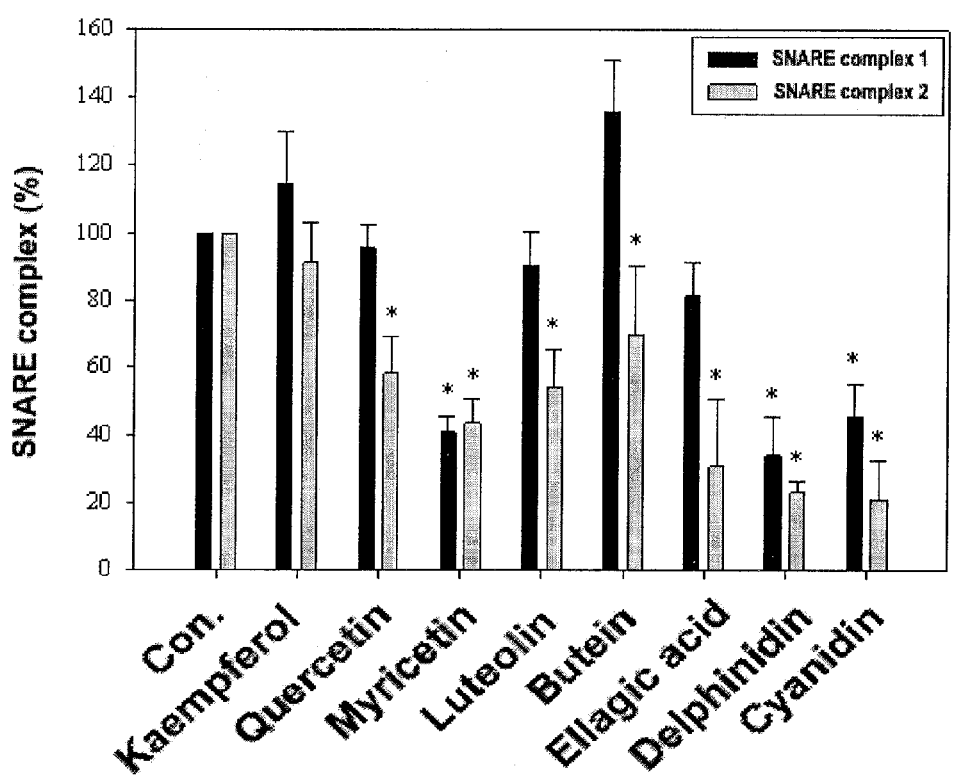
FIG. 7 shows the numerical values of the formation degree of a SNARE complex shown in FIG. 6.
Figure 8:
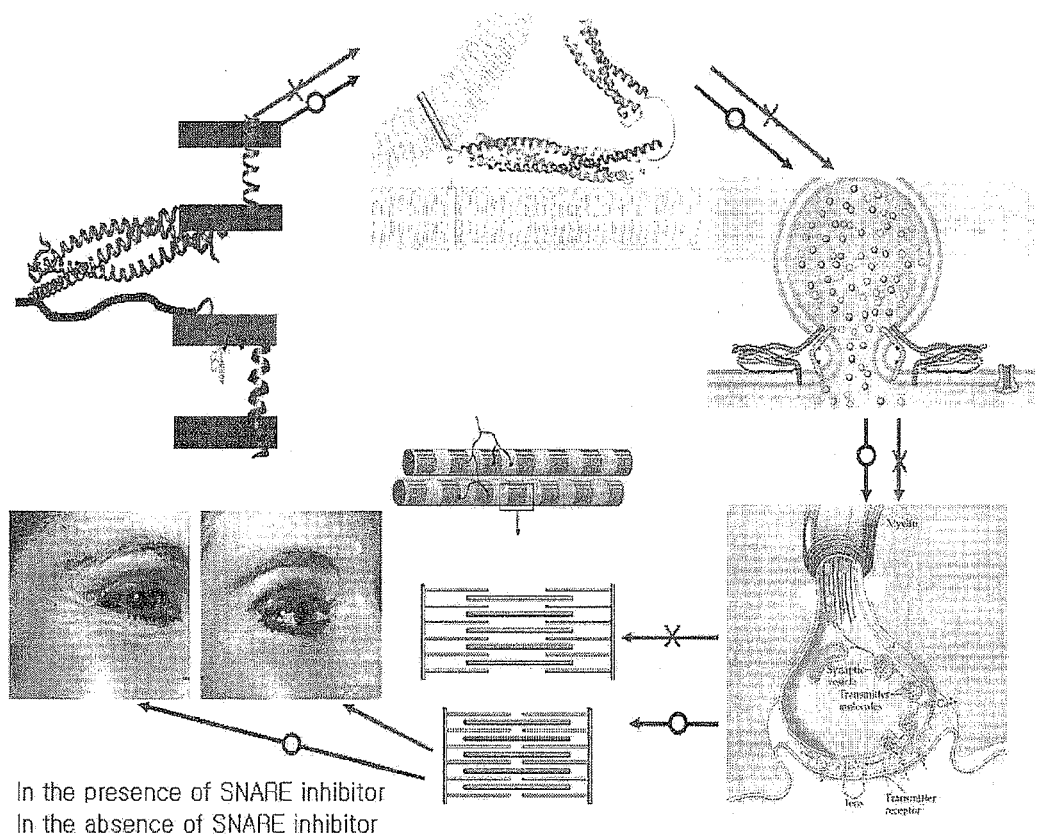
FIG. 8 illustrates an action mechanism of a SNARE inhibitor of the present invention.

FIG. 6 shows Western blot results illustrating that a neurotransmitter release inhibiting effect in a PC12 cell by a polyphenol compound according to the present invention was caused by inhibiting the formation of a SNARE complex. FIG. 7 shows the numerical values of the formation degree of a SNARE complex shown in FIG. 6.

Example 4

Wrinkle Reducing Effect

In this Example, a wrinkle reducing effect was tested.

Each formulation was tested by 20 people between the ages of 20 to 40. Each examinee applied Formulation Examples 1 and 2 to an area around the eyes two times a day, and then, the area around eyes was observed. A replica was prepared with silicon rubber (Silflo), and image analysis was carried out by using a skin visiometer (C+K, Germany) on the start day, 30th day, and 60th day from the start day. The determination was performed based on three criteria, such as (1) significant reduction of wrinkles, (2) slight reduction of wrinkles, and (3) no reduction of wrinkles.

Table 5 shows the test results of myricetin from among polyphenol compounds.

TABLE 5

| Formulation | Reduction of wrinkle (1) | Slight reduction of wrinkle (2) | No ffect (3) |
|---|---|---|---|
| Formulation Example 1 | 5 | 10 | 5 |
| Formulation Example 2 | 5 | 8 | 7 |

Formulation Example 1

Cosmetic Composition 1

From among cosmetics including myricetin, formulation examples of astringent (skin lotion) are as follows.

TABLE 6

| Substance | Content (wt %) |
|---|---|
| 1. myricetin | 0.05-2.5 |
| 2. glycerin | 3.0 |
| 3. butylene glycol | 2.0 |
| 4. propylene glycol | 2.0 |
| 5. polyoxyethylene(60) hydrogenated Caster Oil | 1.0 |
| 6. ethanol | 10.0 |
| 7. triethanolamine | 0.1 |
| 8. preservative | Minute amount |
| 9. colorant | Minute amount |
| 10. Fragrance | Minute amount |
| 11. purified water | Balance |

2, 3, 4, and 8 were sequentially charged in 11, and were dissolved through agitation. Then, 5 was melted through heating at about 60° C. and 10 was charged, and then, the mixture was agitated and charged in 11. Finally, 1, 6, 7, and 9 were charged, and the mixture was matured through sufficient agitation.

Formulation Example 2

Cosmetic Composition 2

From among cosmetics including particles impregnated with myricetin, formulation examples of nutrition lotion are as follows.

TABLE 7

| Substance | Content (wt %) |
|---|---|
| 1. myricetin | 0.05-2.5 |
| 2. Beeswax | 1.0 |
| 3. polysorbate | 1.5 |
| 4. sorbitan sesquioleate | 0.5 |
| 5. liquid paraffin | 5.0 |
| 6. squalene | 5.0 |
| 7. sorbitan stearate | 1.00 |
| 8. glyceryl stearate/PEG-400 stearate | 1.00 |
| 9. lipophilic glyceryl monostearate | 0.50 |
| 10. stearate | 1.50 |
| 11. butylene glycol | 5.00 |
| 12. propylene glycol | 5.00 |
| 13. carboxylic vinyl polymer | 0.1 |
| 14. triethanolamine | 0.2 |
| 15. Preservative | Minute amount |
| 16. colorant | Minute amount |
| 17. fragrance | Minute amount |
| 18. purified water | Balance |

11, 12, 13, 15, and 18 were mixed/agitated and heated at 8085° C., and an emulsifier applied to a preparation unit was activated. Then, 2, 3, 4, 5, 6, 7, 8, 9, 10, and 14 were heated at 80~85° C., charged, and emulsified. After the emulsification, agitation was carried out by using an agitator. Then, when the temperature was cooled to 50° C., 17 was charged, when the temperature was cooled to 45° C., 16 was charged, and when the temperature was cooled to 35° C., 1 was charged. Next, after cooling to 25° C., the mixture was matured.

In the composition, substances appropriate for a cosmetic composition were mixed in a preferred mixing ratio, but the present invention is not limited to the ratio.

Formulation Example 3

Pharmaceutical Composition

Formulation examples of ointment including particles impregnated with myricetin are as follows.

TABLE 8

| Substance | Content (wt %) |
| --- | --- |
| myricetin | 0.03 |
| white petroleum jelly (pharmaceutical grade) | 90.6 |
| silica | 9.18 |

Formulation Example 4

Pharmaceutical Composition 2

Formulation examples of oral suspension (in 10 ml medicine bottle) including particles impregnated with myricetin are as follows.

TABLE 9

| Substance | Content (wt %) |
| --- | --- |
| myricetin | 0.20 g |
| glycerol | 1.00 g |
| 70% sorbitol | 1.00 g |
| sodium saccharinate | 0.01 g |
| methyl p-hydroxybenzoate | 0.08 g |
| fragrance | Quantum satis |
| purified water | 5 ml |

Formulation Example 5

Pharmaceutical Composition 3

Formulation examples of spray including myricetin are as follows.

Respective substances were mixed based on the content as noted in Table 8 to obtain a solution A and a solution B. The two solutions were mixed and were homogenized at 1,200 rpm by using the Ekato mixer. Then, after the each mixed solution was emulsified, the solution was stored in a maturation tank for 10 days after fine filtering. A spray was prepared by injecting 50 ml of the matured liquid into an aluminum aerosol spray vessel, and charging liquefied petroleum gas (LPG) in such a manner that the contents of the vessel has a pressure of 3 kg/ad.

TABLE 10

| Substance | Content (wt %) |
| --- | --- |
| myricetin | 20.0 |
| distilled water | 40 |
| propylene glycol | 3 |
| glycerin | 2.5 |
| sorbitol | 1 |
| lubragel | 1 |
| ethanol | 30 |
| HCO-60 | 2.5 |

The present invention has been described with reference to a preferred embodiment thereof, but it will be understood that changes, obvious to those skilled in the art, may be made within the scope and spirit of the appended claims.

The invention claimed is:

1. A method for reducing skin-wrinkles by inhibiting formation of a SNARE complex and by modulating release of a neurotransmitter, the method comprising administering to a subject in need thereof a composition comprising at least one polyphenol compound selected from the group consisting of kaempferol, quercetin, myricetin, luteolin, delphinidin, cyanidin, butein, and ellagic acid, as an active ingredient.

2. The method as claimed in claim 1, wherein the composition is administered in a formulation selected from the group consisting of solution, suspension, emulsion, paste, gel, cream, lotion, powder, soap, surfactant containing cleaning, oil, powder foundation, emulsion foundation, wax foundation, and spray.

3. The method as claimed in claim 1, wherein an amount of said at least one polyphenol compound ranges from 0.0001 to 50.0 wt % based on a total weight of the composition.

* * * * *